(12) United States Patent
Nishino et al.

(10) Patent No.: US 10,358,395 B2
(45) Date of Patent: Jul. 23, 2019

(54) METHOD FOR PRODUCING BUTADIENE AND DEVICE FOR PRODUCING BUTADIENE

(71) Applicant: SEKISUI CHEMICAL CO., LTD., Osaka (JP)

(72) Inventors: Tomoaki Nishino, Tsukuba (JP); Toshihito Miyama, Tsukuba (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 15/509,059

(22) PCT Filed: Sep. 16, 2015

(86) PCT No.: PCT/JP2015/076254
§ 371 (c)(1),
(2) Date: Mar. 6, 2017

(87) PCT Pub. No.: WO2016/043209
PCT Pub. Date: Mar. 24, 2016

(65) Prior Publication Data
US 2017/0260112 A1    Sep. 14, 2017

(30) Foreign Application Priority Data

Sep. 16, 2014 (JP) ................. 2014-188263
Sep. 16, 2014 (JP) ................. 2014-188264

(51) Int. Cl.
| | |
|---|---|
| *C07C 1/20* | (2006.01) |
| *C07C 1/207* | (2006.01) |
| *C07C 29/151* | (2006.01) |
| *C07C 45/49* | (2006.01) |
| *B01J 23/656* | (2006.01) |
| *B01J 23/80* | (2006.01) |
| *C07C 29/36* | (2006.01) |
| *C07C 27/06* | (2006.01) |
| *C07B 61/00* | (2006.01) |

(52) U.S. Cl.
CPC ......... *C07C 1/2076* (2013.01); *B01J 23/6562* (2013.01); *B01J 23/80* (2013.01); *C07C 1/20* (2013.01); *C07C 27/06* (2013.01); *C07C 29/151* (2013.01); *C07C 29/1518* (2013.01); *C07C 29/36* (2013.01); *C07C 45/49* (2013.01); *B01J 23/656* (2013.01); *C07B 61/00* (2013.01); *C07C 2521/08* (2013.01); *C07C 2523/06* (2013.01); *C07C 2523/72* (2013.01); *C07C 2523/80* (2013.01); *C07C 2523/83* (2013.01)

(58) Field of Classification Search
CPC ..... C07C 29/157; C07C 29/159; C07C 31/04; C07C 31/08; C07C 1/2076; C07C 2521/08; C07C 2523/80; C07C 29/151; C07C 29/36; C07C 45/49; B01J 31/02; B01J 23/6562; B01J 23/80
See application file for complete search history.

(56) References Cited

U.S. PATENT DOCUMENTS

| | | | |
|---|---|---|---|
| 2,506,065 | A | 5/1950 | Clark |
| 3,970,713 | A | 7/1976 | Scharfe et al. |
| 2016/0376206 | A1* | 12/2016 | Dastillung ............. C07C 1/20 585/327 |

FOREIGN PATENT DOCUMENTS

| | | | |
|---|---|---|---|
| EP | 0 361 372 | | 4/1990 |
| EP | 2 581 360 | | 4/2013 |
| JP | 2013-121939 | * | 2/2013 |
| JP | 2013-121939 | | 6/2013 |
| WO | 2013/125389 | | 8/2013 |
| WO | 2014/199349 | | 12/2014 |

OTHER PUBLICATIONS

International Search Report dated Dec. 28, 2015 in International (PCT) Application No. PCT/JP2015/076254.
Jones et al., "Investigations into the conversion of ethanol into 1,3-butadiene", Catalysis Science & Technology, Iss. 1, 2011, pp. 267-272.
De Baerdemaeker et al., "Bimetallic Zn and Hf on Silica Catalysts for the Conversion of Ethanol to 1, 3-Butadiene", ACS Catalysis, vol. 5, Issue 6, 2015, pp. 3393-3397.
Extended European Search Report dated Apr. 26, 2018 in European Application No. 15841605.7.

* cited by examiner

*Primary Examiner* — Sharon Pregler
(74) *Attorney, Agent, or Firm* — Wenderoth, Lind & Ponack, L.L.P.

(57) ABSTRACT

A method for producing butadiene, the method including: a first synthesis step of bringing a mixed gas containing hydrogen and carbon monoxide into contact with a first catalyst to obtain a primary product containing ethanol as an intermediate; and a second synthesis step of bringing the primary product into contact with a second catalyst to obtain butadiene.

4 Claims, 1 Drawing Sheet

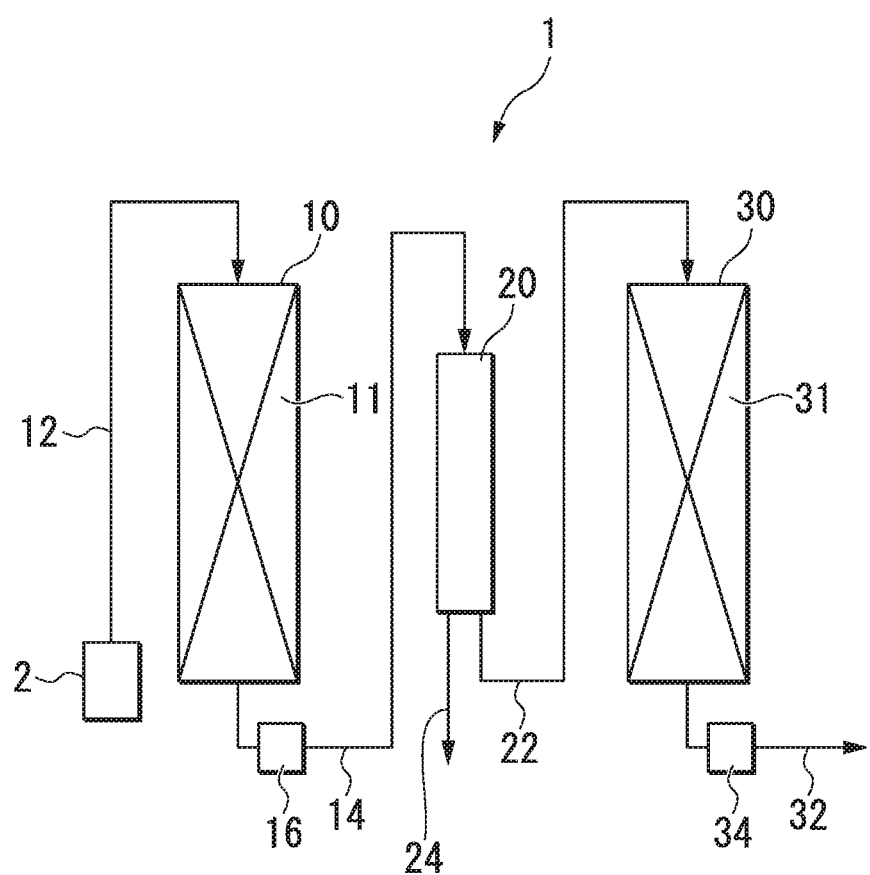

METHOD FOR PRODUCING BUTADIENE AND DEVICE FOR PRODUCING BUTADIENE

TECHNICAL FIELD

The present invention relates to a method for producing butadiene and a device for producing butadiene.

Priority is claimed on Japanese Patent Application No. 2014-188263, filed Sep. 16, 2014, and Japanese Patent Application No. 2014-188264, filed Sep. 16, 2014, the contents of which are incorporated herein by reference.

BACKGROUND ART

Butadiene such as 1,3-butadiene has been used as a raw material of styrene-butadiene rubber (SBR) and the like.

In general, butadiene is purified from a C4 fraction produced as a by-product when synthesizing ethylene from petroleum.

In recent years, bioethanol synthesized from raw materials derived from biomass has attracted attention as an alternative to petroleum.

For example, in Patent Document 1, a method for producing butadiene in which butadiene is synthesized from ethanol (and acetaldehyde) by bringing ethanol (and acetaldehyde) into contact with a specific catalyst has been proposed. The invention of Patent Document 1 attempts to improve the production efficiency of butadiene by increasing the selectivity of butadiene.

PRIOR ART LITERATURE

Patent Documents

[Patent Document 1] International Publication No. 2013/125389

DISCLOSURE OF INVENTION

Problems to be Solved by the Invention

Raw material ethanol such as bioethanol is usually stored in the form of a liquid. Therefore, in the invention described in Patent Document 1, it is necessary to gasify the raw material ethanol and bring the gasified ethanol into contact with the catalyst. That is, when butadiene is produced from ethanol, the energy for gasifying ethanol is required. For this reason, a method for producing butadiene from ethanol is required to further improve energy efficiency.

Further, in the case of producing ethanol from biomass, ethanol is usually purified by subjecting the product containing ethanol to a distillation treatment or the like. Also in the case of producing acetaldehyde from biomass, acetaldehyde is purified by subjecting the product containing acetaldehyde to a distillation treatment or the like. Then, butadiene is synthesized using purified ethanol and purified acetaldehyde.

Therefore, in the invention described in Patent Document 1, the step of producing purified ethanol and the step of producing purified acetaldehyde are provided separately, and as these production steps are present, the production efficiency of butadiene is low.

Accordingly, the present invention aims to provide a method for producing butadiene that can further enhance the energy efficiency and production efficiency.

Means for Solving the Problem

A method for producing butadiene according to the present invention is characterized by including: a first synthesis step of bringing a mixed gas containing hydrogen and carbon monoxide into contact with a first catalyst to obtain a primary product containing ethanol as an intermediate; and a second synthesis step of bringing the aforementioned primary product into contact with a second catalyst to obtain butadiene. It is preferable that the aforementioned primary product further contains acetaldehyde as an intermediate. It is preferable that the molar ratio of the aforementioned primary product represented by ethanol/acetaldehyde is from 5/1 to 1/5. It is preferable that the aforementioned first synthesis step obtains the aforementioned primary product as a gas and the aforementioned second synthesis step brings the aforementioned primary product as it is in a gaseous form into contact with the aforementioned second catalyst, and a first purification step of removing substances other than the aforementioned intermediate from the aforementioned primary product may be provided between the aforementioned first synthesis step and the aforementioned second synthesis step.

A device for producing butadiene according to the present invention is characterized by including: a first reaction tube filled with a first catalyst; and a second reaction tube filled with a second catalyst, wherein the aforementioned first catalyst synthesizes a primary product containing ethanol or ethanol and acetaldehyde as an intermediate from a mixed gas containing hydrogen and carbon monoxide; the aforementioned second catalyst synthesizes butadiene from the aforementioned intermediate; and the aforementioned second reaction tube is provided downstream of the aforementioned first reaction tube and brings the aforementioned primary product into contact with the aforementioned second catalyst. A first purifier for removing substances other than the aforementioned intermediate from the aforementioned primary product may be provided between the aforementioned first reaction tube and the aforementioned second reaction tube.

Effects of the Invention

According to the method for producing butadiene of the present invention, the energy efficiency and the production efficiency of butadiene can be further enhanced.

BRIEF DESCRIPTION OF DRAWINGS

FIG. 1 is a schematic diagram of a device for producing butadiene according to an embodiment of the present invention.

DESCRIPTION OF EMBODIMENTS

Throughout this specification, the term "butadiene" refers to 1,3-butadiene, unless otherwise specified.

(Butadiene Production Device)

A device for producing butadiene (butadiene production device) of the present invention is equipped with a first reaction tube and a second reaction tube provided downstream of the first reaction tube.

An embodiment of the butadiene production device will be described with reference to FIG. 1.

A butadiene production device 1 of FIG. 1 is provided with a mixed gas supply source 2, a first reaction tube 10, a first purifier 20 and a second reaction tube 30.

The mixed gas supply source 2 and the first reaction tube are connected by a pipe 12.

The first reaction tube 10 and the first purifier 20 are connected by a pipe 14. The pipe 14 is provided with a first pressure control unit 16. A discharge pipe 24 is connected to the first purifier 20. The discharge pipe 24 is connected to a recovery machine (not shown). The first purifier 20 and the second reaction tube 30 are connected by a pipe 22. A pipe 32 is connected to the second reaction tube 30. The pipe 32 is provided with a second pressure control unit 34.

The mixed gas supply source 2 may be any source as long as it can supply a mixed gas containing hydrogen and carbon monoxide.

Examples of the mixed gas supply source 2 include a cylinder containing a mixed gas, a combination of a cylinder containing hydrogen and a cylinder containing carbon monoxide, and the like.

The mixed gas, hydrogen and carbon monoxide contained in the cylinder may be, for example, those prepared from natural gas or coal, may be a biomass gas or the like obtained by gasifying biomass, or may be those obtained by gasifying organic waste such as waste plastics, waste paper and waste clothing (hereinafter, may be referred to as recycle gas). The biomass gas and the recycle gas can be obtained by a conventionally known method such as, for example, a method of heating (e.g., at 800 to 1,000° C.) the pulverized biomass or organic waste in the presence of water vapor.

Further, for example, the mixed gas supply source 2 may be a gasification furnace or the like that generates biomass gas or recycle gas. By using the gasification furnace as the mixed gas supply source 2, it is possible to perform a step of generating a mixed gas from biomass or the like and a step of producing butadiene from the mixed gas using a single device.

As the gasification furnace, for example, any gasification furnace capable of generating a mixed gas by heating biomass or organic waste in the presence of water vapor may be used. As the gasification furnace, a gasification furnace of a floating external thermal gasification system is preferable. The gasification furnace of a floating external thermal gasification system is preferable in that the ratio of hydrogen and carbon monoxide can be easily adjusted and there are a few impurities other than hydrogen and carbon monoxide.

When the mixed gas supply source 2 is a gasification furnace, it is preferable to provide a gas purifier between the mixed gas supply source 2 and the first reaction tube 10. By providing a gas purifier, impurities such as tar components, sulfur components, nitrogen components, chlorine components and moisture are removed from the biomass gas and the recycle gas.

As the gas purifier, for example, a gas purifier of any type known in the art, such as a wet method or a dry method, is employed. Examples of the wet method include a sodium hydroxide method, an ammonia absorption method, a lime/gypsum method and a magnesium hydroxide method, and examples of the dry method include an activated carbon adsorption method such as a pressure swing adsorption (PSA) method, and an electron beam method.

The pipe 12 is preferably made of a material that is inert to the mixed gas, and examples thereof include a pipe made of stainless steel or the like.

The first reaction tube 10 is one in which a first catalyst is filled and a first reaction bed 11 is formed. The first reaction tube 10 is preferably made of a material that is inert to a mixed gas, ethanol and acetaldehyde. Further, the first reaction tube 10 preferably has a shape that can withstand heating at about 100 to 500° C. or pressurization at about 10 MPa. As the reaction tube 1, for example, a substantially cylindrical member made of stainless steel can be mentioned.

The first reaction bed 11 may be any one of a fixed bed, a moving bed, a fluidized bed and the like.

The first catalyst may be any catalyst as long as it can synthesize ethanol as an intermediate, or ethanol and acetaldehyde from hydrogen and carbon monoxide. By using the first catalyst, a primary product containing the aforementioned intermediate (for example, ethanol-containing gas containing ethanol) can be obtained from the mixed gas.

As the first catalyst, a so-called supported catalyst in which a hydrogenation-active metal is supported on a porous carrier can be mentioned. Further, as the first catalyst, a hydrogenation-active metal or a combination of a hydrogenation-active metal and a co-active metal to be described later (hereinafter, the metal used for the first or second catalyst is generally referred to as a catalytic metal in some cases) may be used. As the first catalyst, a supported catalyst is preferable. If a supported catalyst is used, it is easy to control the ethanol concentration and the ratio of ethanol and acetaldehyde in the product.

The material of the porous carrier is not particularly limited, and examples thereof include silica, zirconia, titania and magnesia. Among them, silica is preferable because a variety of products having different specific surface areas and pore diameters can be procured in the market.

Although the size of the porous carrier is not particularly limited, for example, as long as it is a porous carrier of silica, one having a particle diameter of 0.5 to 5,000 μm is preferable. The particle size of the porous carrier is adjusted by sieving.

In addition, it is preferable that the porous carrier has a particle size distribution as narrow as possible.

Although the total pore volume in the porous carrier (total pore volume) is not particularly limited, for example, it is preferably from 0.01 to 1.0 mL/g, and more preferably from 0.1 to 0.8 mL/g. If the total pore volume is less than the above lower limit value, the specific surface area of the porous carrier becomes insufficient, the supported amount of the catalytic metal becomes insufficient, and the CO conversion may be reduced. When the total pore volume exceeds the above upper limit value, the diffusion rate of the mixed gas as a raw material becomes too fast, the contact time between the catalyst and the mixed gas becomes insufficient, and the selectivity of the aforementioned intermediate such as ethanol may become low.

The total pore volume is a value measured by a water titration method. The water titration method is a method of adsorbing water molecules on the surface of a porous carrier and measuring the pore distribution from the condensation of molecules.

It should be noted that the term "CO conversion" means the percentage occupied by the number of moles of CO consumed out of the number of moles of CO in the mixed gas.

The term "selectivity" refers to the percentage occupied by the number of moles of C converted to a specific compound out of the number of moles of CO consumed in the mixed gas. For example, according to the following formula (α), the selectivity of ethanol is 100 mol %. On the other hand, according to the following formula (β), the selectivity of ethanol is 50 mol % and the selectivity of acetaldehyde is also 50 mol %.

$$4H_2 + 2CO \rightarrow CH_3CH_2OH + H_2O \tag{$\alpha$}$$

$$7H_2 + 4CO \rightarrow C_2H_5OH + CH_3CHO + 2H_2O \tag{$\beta$}$$

The average pore diameter of the porous carrier is, for example, preferably from 0.1 to 8 nm, and more preferably from 3 to 6 nm. If the average pore diameter is less than the above lower limit value, there is a possibility that the supported amount of the catalytic metal decreases and the CO conversion decreases. When the average pore diameter exceeds the above upper limit value, the diffusion rate of the mixed gas becomes too fast, the contact time between the catalytic metal and the mixed gas becomes insufficient and the selectivity of the aforementioned intermediate such as ethanol becomes low. That is, if the average pore diameter is within the above range, the contact time between the catalytic metal and the mixed gas becomes a time that is suitable for producing the aforementioned intermediate such as ethanol efficiently.

The average pore diameter is a value measured by the following method. When the average pore diameter is 0.1 nm or more and less than 10 nm, the average pore diameter is calculated from the total pore volume and the BET specific surface area. When the average pore diameter is 10 nm or more, the average pore diameter is measured by a mercury intrusion porosimeter.

Here, the total pore volume is a value measured by a water titration method, and the BET specific surface area is a value calculated from the adsorption amount and the pressure at that time, using nitrogen as an adsorption gas.

In the mercury porosimetry, mercury is pressurized and press-fitted into the pores of a porous carrier, and the average pore diameter is calculated from the pressure and the amount of press-fitted mercury.

Although the specific surface area of the porous carrier is not particularly limited, for example, it is preferably from 1 to 1,000 m$^2$/g, and more preferably from 10 to 800 m$^2$/g. If the specific surface area is equal to or more than the above lower limit value, the supported amount of the catalytic metal becomes sufficient and the CO conversion is further enhanced. If the specific surface area is equal to or less than the above upper limit value, the diffusion rate of the mixed gas becomes more appropriate, and the selectivity of the aforementioned intermediate such as ethanol is further enhanced.

The specific surface area is a BET specific surface area measured by a BET-type gas adsorption method using nitrogen as an adsorption gas.

The product of the total pore volume and the specific surface area in the porous carrier is preferably from 1 to 1,000 mL·m$^2$/g$^2$, and more preferably from 100 to 500 mL·m$^2$/g$^2$. If the product is equal to or more than the above lower limit value, the supported amount of the catalytic metal becomes sufficient and the CO conversion is further enhanced. If the product is equal to or less than the above upper limit value, the diffusion rate of the mixed gas becomes more appropriate, and the selectivity of the aforementioned intermediate such as ethanol is further enhanced.

As the hydrogenation-active metal, any metal conventionally known to be capable of synthesizing ethanol (and acetaldehyde) from a mixed gas may be used, and examples thereof include alkali metals such as lithium and sodium; elements belonging to Group 7 in the periodic table such as manganese and rhenium; elements belonging to Group 8 in the periodic table such as ruthenium; elements belonging to Group 9 in the periodic table such as cobalt and rhodium; and elements belonging to Group 10 in the periodic table such as nickel and palladium.

Any one of these hydrogenation-active metals may be used alone, or two or more of these may be used in combination. For example, as the hydrogenation-active metal, from the viewpoint of further improving the CO conversion and further improving the selectivity of the aforementioned intermediate such as ethanol, combinations of rhodium or ruthenium, an alkali metal and another hydrogenation-active metal, such as a combination of rhodium, manganese and lithium and a combination of ruthenium, rhenium and sodium are preferred.

The supported amount of the hydrogenation-active metal in the first catalyst is determined in consideration of the type of the hydrogenation-active metal, the material of the porous carrier, and the like.

When an alkali metal is used as the hydrogenation-active metal, the supported amount of the hydrogenation-active metal is preferably from 0.001 to 30 parts by mass, and more preferably from 0.125 to 10 parts by mass, with respect to 100 parts by mass of the porous carrier. If the amount is less than the above lower limit value, the supported amount of the hydrogenation-active metal is too small, which may result in a lower CO conversion, and if the amount exceeds the above upper limit value, the hydrogenation-active metal cannot be uniformly and highly dispersed, and the CO conversion and the selectivity of the aforementioned intermediate such as ethanol may be lowered.

When an element belonging to Group 7 in the periodic table is used as the hydrogenation-active metal, the supported amount of the hydrogenation-active metal is preferably from 0.001 to 30 parts by mass, and more preferably from 0.25 parts by mass to 10 parts by mass, with respect to 100 parts by mass of the porous carrier. If the amount is less than the above lower limit value, the supported amount of the hydrogenation-active metal is too small, which may result in a lower CO conversion, and if the amount exceeds the above upper limit value, the hydrogenation-active metal cannot be uniformly and highly dispersed, and the CO conversion and the selectivity of the aforementioned intermediate such as ethanol may be lowered.

When an element belonging to Group 8 to Group 10 in the periodic table is used as the hydrogenation-active metal, the supported amount of the hydrogenation-active metal is preferably from 0.1 to 30 parts by mass, and more preferably from 1 to 10 parts by mass, with respect to 100 parts by mass of the porous support. If the amount is less than the above lower limit value, the supported amount of the hydrogenation-active metal is too small, which may result in a lower CO conversion, and if the amount exceeds the above upper limit value, the hydrogenation-active metal cannot be uniformly and highly dispersed, and the CO conversion and the selectivity of the aforementioned intermediate such as ethanol may be lowered.

When two or more types of hydrogenation-active metals are used in combination, the supported amount of the hydrogenation-active metal is determined in consideration of the composition, the type of the porous carrier, and the like. For example, if the porous carrier is silica, the supported amount of the hydrogenation-active metal is preferably from 0.05 to 30 parts by mass, and more preferably from 1 to 10 parts by mass, with respect to 100 parts by mass of the porous carrier. If the amount is less than the above lower limit value, there is a possibility that the CO conversion is lowered, and if the amount exceeds the above upper limit value, the hydrogenation-active metal cannot be uniformly and highly dispersed, and the CO conversion and the selectivity of the aforementioned intermediate such as ethanol may be lowered.

The supported state of the hydrogenation-active metal in the first catalyst is not particularly limited, and for example, it may be a state in which a powdered metal is supported on the porous carrier, or it may be a state of being supported on the porous carrier in the form of a metal element. In particular, a state of being supported on the porous carrier in the form of a metal element is preferable. As long as it is in a state of being supported on the porous carrier in the form of a metal element, the contact area with the mixed gas becomes large, and the CO conversion and the selectivity of the aforementioned intermediate such as ethanol can be further enhanced.

In addition to the hydrogenation-active metal, a co-active metal may be supported on the first catalyst.

Examples of the co-active metal include titanium, magnesium and vanadium. By supporting these co-active metals, the first catalyst can further increase the CO conversion and the selectivity of the aforementioned intermediate such as ethanol.

The supported amount of the co-active metal in the first catalyst is determined in consideration of the type of the co-active metal, the type of the hydrogenation-active metal, and the like. For example, the supported amount is preferably from 0.01 to 20 parts by mass, and more preferably from 1 to 10 parts by mass, with respect to 100 parts by mass of the porous carrier. If it is less than the above lower limit value, the supported amount of the co-active metal is too small, making it difficult to further improve the CO conversion and the selectivity of the aforementioned intermediate such as ethanol. If it exceeds the above upper limit value, the surface of the porous carrier is excessively covered with the co-active metal, making it difficult to improve the CO conversion and the selectivity of the aforementioned intermediate such as ethanol.

The supported state of the co-active metal in the first catalyst is not particularly limited, and for example, it may be a state in which a powdered metal is supported on the porous carrier, or it may be a state of being supported on the porous carrier in the form of a metal element. In particular, a state of being supported on the porous carrier in the form of a metal element is preferable. As long as it is in a state of being supported on the porous carrier in the form of a metal element, the contact area with the mixed gas becomes large, and the CO conversion and the selectivity of the aforementioned intermediate such as ethanol can be further enhanced.

The supported amount of the catalytic metal in the first catalyst is determined in consideration of the type and composition of the catalytic metal, the material of the porous carrier, and the like. For example, the supported amount is preferably from 0.05 to 30 parts by mass, and more preferably from 1 to 10 parts by mass, with respect to 100 parts by mass of the porous carrier. If it is less than the above lower limit value, the supported amount of the catalytic metal is too small, making it difficult to improve the CO conversion and the selectivity of the aforementioned intermediate such as ethanol. If it exceeds the above upper limit value, the amount of the co-active metal becomes excessive and the hydrogenation-active metal cannot be uniformly and highly dispersed, making it difficult to further improve the CO conversion and the selectivity of the aforementioned intermediate such as ethanol.

As the first catalyst, a rhodium-based catalyst having a composition represented by the following formula (I) is preferable.

$$aA \cdot bB \cdot cC \cdot dD \quad \text{(I)}$$

In the formula (I), A represents rhodium, B represents manganese, C represents an alkali metal, D represents a co-active metal, a, b, c and d represent mole fractions, and a+b+c+d=1.

In the formula (I), a is preferably from 0.053 to 0.98, more preferably from 0.24 to 0.8, and even more preferably from 0.32 to 0.67. If it is less than the above lower limit value, the content of rhodium may be too small and the CO conversion may not be sufficiently increased. If it exceeds the above upper limit value, the content of other metals becomes too small and the CO conversion may not be sufficiently increased.

In the formula (I), b is preferably from 0.0006 to 0.67, more preferably from 0.033 to 0.57, and even more preferably from 0.089 to 0.44. If it is less than the above lower limit value, the content of manganese may be too small and the CO conversion may not be sufficiently increased. If it exceeds the above upper limit value, the content of other metals becomes too small and the CO conversion may not be sufficiently increased.

In the formula (I), c is preferably from 0.00056 to 0.51, more preferably from 0.026 to 0.42, and even more preferably from 0.075 to 0.33. If it is less than the above lower limit value, the content of the alkali metal may be too small and the CO conversion may not be sufficiently increased. If it exceeds the above upper limit value, the content of other metals becomes too small and the CO conversion may not be sufficiently increased.

In the formula (I), d may be 0 (that is, a co-active metal is not contained) or may be greater than 0 (that is, a co-active metal is contained). In the case of containing a co-active metal, d is preferably from 0.0026 to 0.94, more preferably from 0.02 to 0.48, and even more preferably from 0.039 to 0.25. If it is less than the above lower limit value, the content of the co-active metal may be too small and the CO conversion may not be sufficiently increased. If it exceeds the above upper limit value, the content of other metals becomes too small and the CO conversion may not be sufficiently increased.

The first catalyst is produced in accordance with a conventionally known method for producing a supported catalyst. As a method for producing the first catalyst, for example, an impregnation method, an ion exchange method and the like can be mentioned, and among them, an impregnation method is preferable.

By using the impregnation method, the catalytic metal is more uniformly dispersed in the resulting first catalyst, the contact efficiency with the mixed gas can be further enhanced, and the CO conversion and the selectivity of the aforementioned intermediate such as ethanol can be further enhanced.

As the raw material compound of the catalytic metal used for preparing the first catalyst, those conventionally used, as the compounds of the catalytic metals, for preparing a metal catalyst, including inorganic salts such as oxides, chlorides, sulfides, nitrates and carbonates, organic salts or chelate compounds such as oxalates, acetylacetonate salts, dimethylglyoxime salts and ethylenediamine acetate salts, carbonyl compounds, cyclopentadienyl compounds, amine complexes, alkoxide compounds, alkyl compounds and the like can be mentioned. Among them, chlorides or sulfides are preferable.

The impregnation method will be described. First, a raw material compound of a hydrogenation-active metal and, if necessary, a raw material compound of a co-active metal are dissolved in a solvent such as water, methanol, ethanol, tetrahydrofuran, dioxane, hexane, benzene or toluene, and the porous carrier is immersed in the obtained solution (impregnating solution) or the like, thereby allowing the impregnating solution to adhere to the porous carrier. After sufficiently impregnating the impregnating solution into the pores of the porous carrier, the solvent is evaporated to form a catalyst. In the impregnation method, the mass ratio of each catalytic metal in the impregnating solution is the mass ratio of each catalytic metal supported on the first catalyst. Therefore, by producing the first catalyst by the impregnation method, it is possible to easily control the mass ratio of each catalytic metal in the first catalyst.

As a method of impregnating the porous carrier with the impregnating solution, a method of impregnating a carrier with a solution in which all the raw material compounds are dissolved (simultaneous method), a method of preparing solutions by separately dissolving each raw material compound, and sequentially impregnating the carrier with each solution (sequential method), and the like can be mentioned.

As the sequential method, for example, a method in which a porous carrier is impregnated with a solution (primary impregnating solution) containing a co-active metal (primary impregnation step); the resultant is dried to obtain a primary carrier in which the co-active metal is supported on the porous carrier (primary loading step); then impregnating the primary carrier with a solution (secondary impregnating solution) containing a hydrogenation-active metal (secondary impregnation step); and drying the resultant (secondary loading step), can be mentioned. As described above, by loading the co-active metal on the porous carrier and then loading the hydrogenation-active metal on the carrier, the first catalyst becomes one in which the catalytic metal is more highly dispersed, and the CO conversion and the selectivity of the aforementioned intermediate such as ethanol can be further enhanced.

The primary loading step may be performed, for example, by a method in which the porous carrier impregnated with the primary impregnating solution is dried (primary drying operation) and the resultant is calcined by heating at an arbitrary temperature (primary calcination operation).

The drying method in the primary drying operation is not particularly limited, and, for example, a method of heating the porous carrier impregnated with the primary impregnating solution at an arbitrary temperature can be mentioned. The heating temperature in the primary drying operation may be any temperature as long as the solvent of the primary impregnating solution can be evaporated, and it is from 80 to 120° C. if the solvent is water. The heating temperature in the primary calcination operation is, for example, from 300 to 600° C. By performing the primary calcination operation, among the components contained in the raw material compound of the co-active metal, the components that do not contribute to the catalytic reaction are sufficiently volatilized to further enhance the catalytic activity.

The secondary loading step may be performed, for example, by a method in which the primary carrier impregnated with the secondary impregnating solution is dried (secondary drying operation) and further calcined by heating at an arbitrary temperature (secondary calcination operation).

The drying method in the secondary drying operation is not particularly limited, and, for example, a method of heating the primary carrier impregnated with the secondary impregnating solution at an arbitrary temperature can be mentioned. The heating temperature in the secondary drying operation may be any temperature as long as the solvent of the secondary impregnating solution can be evaporated, and it is from 80 to 120° C. if the solvent is water. The heating temperature in the secondary calcination operation is, for example, from 300 to 600° C. By performing the secondary calcination operation, among the components contained in the raw material compound of the hydrogenation-active metal, the components that do not contribute to the catalytic reaction are sufficiently volatilized, and the catalytic activity of the first catalyst can be further enhanced.

The first catalyst prepared by the above-mentioned method is usually subjected to a reduction treatment to be activated. As the reduction treatment, a method of bringing the first catalyst into contact with a gas containing hydrogen is simple and is therefore preferable. At this time, the treatment temperature is set to a temperature at which the hydrogenation-active metal is reduced, and, for example, if the hydrogenation-active metal is rhodium, it is 100° C. or higher, and preferably from 200 to 600° C. In addition, for the purpose of sufficiently dispersing the hydrogenation-active metal, hydrogen reduction may be carried out while raising the temperature gradually or in a stepwise manner from a low temperature. Further, for example, the first catalyst may be subjected to a reduction treatment in the presence of carbon monoxide and water, or in the presence of a reducing agent such as hydrazine, a boron hydride compound or an aluminum hydride compound.

The heating time in the reduction treatment is, for example, preferably from 1 to 10 hours, and more preferably from 2 to 5 hours. If it is less than the above lower limit value, the reduction of the catalytic metal becomes insufficient, and the CO conversion and the selectivity of the aforementioned intermediate such as ethanol may become low. If it exceeds the above upper limit value, the catalytic metal aggregates, the CO conversion and the selectivity of the aforementioned intermediate such as ethanol become low, the energy in the reduction treatment becomes excessive, and economic disadvantage may occur.

The first catalyst may be composed only of a rhodium-based catalyst or a mixture of a rhodium-based catalyst and another catalyst.

Examples of other catalysts include catalysts in which copper alone or copper and a transition metal other than copper are supported on a carrier (hereinafter sometimes referred to as a copper-based catalyst). The copper-based catalyst can convert oxygenates other than ethanol to ethanol. For this reason, by containing the rhodium-based catalyst and the copper-based catalyst, the first catalyst can increase the selectivity of ethanol.

It should be noted that, in this specification, the term "oxygenate" refers to a molecule composed of a carbon atom, a hydrogen atom and an oxygen atom, including alcohols such as methanol, ethanol and propanol, carboxylic acids such as acetic acid, aldehydes such as acetaldehyde, and esters such as methyl formate, ethyl formate, methyl acetate and ethyl acetate.

As the copper-based catalyst, those represented by the following formula (II) are preferred.

$$eE{:}fF \qquad (\mathrm{II})$$

In the formula (II), E represents copper, F represents a transition metal other than copper, e and f represent mole fractions, and e+f=1.

In the formula (II), F is preferably zinc or chromium. One type of F may be used alone, or two or more types thereof may be used in combination.

In the formula (II), e is preferably from 0.5 to 0.9, and more preferably from 0.5 to 0.7. If it is less than the above lower limit value, the content of copper is too small, and the efficiency of converting oxygenates other than ethanol to ethanol may be reduced. If it exceeds the above upper limit value, the content of F becomes too small, and the efficiency of converting oxygenates other than ethanol to ethanol may be reduced.

In the formula (II), f is preferably from 0.1 to 0.5, and more preferably from 0.3 to 0.5. If it is less than the above lower limit value, the content of F is too small, and the efficiency of converting oxygenates other than ethanol to ethanol may be reduced. If it exceeds the above upper limit value, the content of copper becomes too small, and the efficiency of converting oxygenates other than ethanol to ethanol may be reduced.

When the first catalyst contains a rhodium-based catalyst and a copper-based catalyst, it is preferable that the rhodium-based catalyst does not contain copper and the copper-based catalyst does not contain rhodium.

When the first catalyst contains a rhodium-based catalyst and a copper-based catalyst, the mass ratio represented by the formula (copper-based catalyst)/(rhodium-based catalyst) is, for example, preferably 1 or more, more preferably greater than 1, even more preferably greater than 1 and 10 or less, and particularly preferably from 2.5 to 5. If the ratio represented by (copper-based catalyst)/(rhodium-based catalyst) is less than the above lower limit value, there is a possibility that the CO conversion is lowered at an early stage. If the ratio exceeds the above upper limit value, there is a possibility that the production amount of the aforementioned intermediate such as ethanol per unit mass of the first catalyst is reduced, and the production efficiency may be lowered.

The pipe 14 is preferably made of a material that is inert to primary products such as ethanol-containing gas, and examples thereof include a pipe made of stainless steel or the like.

In the present embodiment, the pipe 14 is provided with a first pressure control unit 16. The first pressure control unit 16 may be any unit as long as the pressure in the first reaction tube 10 can be set to an arbitrary pressure, and, for example, a known pressure valve or the like can be mentioned.

The first purifier 20 removes substances other than the aforementioned intermediates (for example, acetic acid, ethyl acetate, unreacted mixed gas, or the like) from the primary products.

As the first purifier 20, for example, an apparatus equipped with a separation membrane can be mentioned. As the separation membrane, for example, a separation membrane for treating acid gas-containing gas described in International Publication No. 2014/080670, a porous support-zeolite membrane composite described in International Publication No. 2013/125661, and the like can be mentioned.

The pipe 22 is preferably made of a material that is inert to the aforementioned intermediate, and examples thereof include a pipe made of stainless steel or the like.

The second reaction tube 30 is one in which a second catalyst is filled and a second reaction bed 31 is formed. The second reaction tube 30 is preferably made of a material that is inert to a mixed gas, ethanol and acetaldehyde. Further, the second reaction tube 30 preferably has a shape to withstand heating at about 100 to 500° C. or pressurization at about 10 MPa. As the second reaction tube 30, for example, a substantially cylindrical member made of stainless steel can be mentioned.

The second reaction bed 31 may be any one of a fixed bed, a moving bed, a fluidized bed and the like.

The second catalyst may be any catalyst as long as it can synthesize butadiene from the aforementioned intermediate (ethanol, or ethanol and acetaldehyde). Examples of the second catalyst include those containing oxides of metals of Groups 4 to 13 of the periodic table and magnesium oxide.

For example, as the second catalyst, those in which a metal of Groups 4 to 13 of the periodic table and magnesium oxide are joined by one or more members selected from magnesia and silica are preferred.

More preferable examples of the second catalyst include those in which tantalum oxide is joined by magnesia and silica ($Ta_2O_5/MgO/SiO_2$ (mass ratio=2/83/15), see International Publication No. 2013/125389); those in which zirconium oxide and zinc oxide are supported on a mixture of magnesium oxide and silica ($ZrZn$—$MgO/SiO_2$ (mass ratio of $MgO/SiO_2$=85/15), see "Matthew D. Jones, Catalysis Communications 49 (2014), p. 25-28"); and those in which hafnium oxide, copper oxide and zinc oxide are supported on silica (($HfCuZn/SiO_2$), see "Dirk E. De Vos, Catalysis 5 (2015), p. 3393-3397").

The second catalyst is produced by a known method.

As a method for producing the second catalyst, for example, a method in which a sol of a catalytic metal is dispersed in a sol obtained by dispersing at least one selected from silica and magnesia to obtain a catalyst sol, and this catalyst sol is calcined, can be mentioned.

The pipe 32 is preferably made of a material that is inert to butadiene, and examples thereof include a pipe made of stainless steel or the like.

In the present embodiment, the pipe 32 is provided with a second pressure control unit 34. The second pressure control unit 34 may be any unit as long as it can set the pressure in the second reaction tube 30 to an arbitrary pressure, and, for example, a known pressure valve or the like can be mentioned.

The butadiene production device 1 may be equipped with a known device, including a gas flow rate control unit for adjusting the flow rate of the gas, such as a mass flow controller. In addition, the butadiene production device 1 may be provided with a device (second purifier) for purifying butadiene on the downstream of the second reaction tube 30. Examples of the device for purifying butadiene include a gas-liquid separator and the like.

(Production Method of Butadiene)

A method for producing butadiene according to the present invention includes: a first synthesis step of bringing a mixed gas containing hydrogen and carbon monoxide into contact with a first catalyst to obtain a primary product containing ethanol as an intermediate; and a second synthesis step of bringing the aforementioned primary product into contact with a second catalyst to obtain butadiene.

An example of the method for producing butadiene according to the present invention will be described using the production device of FIG. 1.

First, the first reaction bed 11 and the second reaction bed 31 are set to have an arbitrary temperature and an arbitrary pressure. A mixed gas is caused to flow into the first reaction tube 10 from the mixed gas supply source 2 via the pipe 12.

The mixed gas flowed into the first reaction tube 10 flows through while coming into contact with the first catalyst of the first reaction bed 11, and a portion thereof becomes ethanol (and acetaldehyde).

While flowing through the first reaction bed 11, the mixed gas generates ethanol and acetaldehyde, for example, by the catalytic reaction represented by the following formulae (1) to (5). In the present invention, the catalytic reactions represented by the formulae (2), (4) and (5) predominantly proceed.

$$2H_2 + 2CO \rightarrow CH_3COOH \tag{1}$$

$$3H_2 + 2CO \rightarrow CH_3CHO + H_2O \tag{2}$$

$$2H_2CH_3COOH \rightarrow CH_3CH_2OH + H_2O \quad (3)$$

$$H_2 + CH_3CHO \rightarrow CH_3CH_2OH \quad (4)$$

$$4H_2 + 2CO \rightarrow CH_3CH_2OH + H_2O \quad (5)$$

In this manner, the mixed gas flows through the first reaction bed 11 and becomes a primary product containing ethanol (or ethanol and acetaldehyde) as an intermediate. In the present embodiment, the primary product is a gas such as ethanol-containing gas. The primary product flows out from the first reaction tube 10 (the processes up to this point constitute the first synthesis step).

The mixed gas contains hydrogen and carbon monoxide as a main component, that is, the total of hydrogen and carbon monoxide in the mixed gas is preferably 50% by volume or more, more preferably 80% by volume or more, even more preferably 90% by volume or more, and may be 100% by volume. The higher the content of hydrogen and carbon monoxide, the higher the production of ethanol (and acetaldehyde).

The volume ratio expressed by hydrogen/carbon monoxide in the mixed gas (hereinafter, sometimes referred to as a $H_2/CO$ ratio) is preferably from 1/5 to 5/1, more preferably from 1/2 to 3/1, and even more preferably from 1/1 to 2.5/1. If the $H_2/CO$ ratio is within the above range, the CO conversion and the selectivity of ethanol (and acetaldehyde) can be further enhanced.

It should be noted that in addition to hydrogen and carbon monoxide, the mixed gas may contain methane, ethane, ethylene, nitrogen, carbon dioxide, water and the like.

The temperature (reaction temperature) at the time of bringing the mixed gas into contact with the first catalyst, in other words, the temperature of the first reaction bed 11 is, for example, preferably from 150 to 450° C., more preferably from 200 to 400° C., and even more preferably from 250 to 350° C. If it is equal to or more than the above lower limit value, the rate of the catalytic reaction can be sufficiently increased, and ethanol (and acetaldehyde) can be produced more efficiently. If it is equal to or less than the above upper limit value, the synthesis reaction of ethanol (and acetaldehyde) will be the main reaction, and the selectivity of ethanol (and acetaldehyde) can also be enhanced.

The pressure (reaction pressure) at the time of bringing the mixed gas into contact with the first catalyst, in other words, the pressure inside the first reaction tube 10 is, for example, preferably from 0.5 to 10 MPa, more preferably from 1 to 7.5 MPa, and even more preferably from 2 to 5 MPa. If it is equal to or more than the above lower limit value, the rate of the catalytic reaction can be sufficiently increased, and ethanol (and acetaldehyde) can be produced more efficiently. If it is equal to or less than the above upper limit value, the synthesis reaction of ethanol (and acetaldehyde) will be the main reaction, and the selectivity of ethanol (and acetaldehyde) can also be enhanced.

The space velocity of the mixed gas in the first reaction bed 11 (the value obtained by dividing the supply amount of gas per unit time by the catalyst amount (in terms of volume)) is, in terms of the standard state, preferably from 10 to 100,000 L/L-catalyst/h, more preferably from 1,000 to 50,000 L/L-catalyst/h, and even more preferably from 3,000 to 20,000 L/L-catalyst/h. The space velocity is appropriately adjusted in consideration of the reaction pressure, the reaction temperature, and the composition of the mixed gas as a raw material.

It is preferable that the aforementioned primary product contains acetaldehyde in addition to ethanol as an intermediate. By subjecting acetaldehyde together with ethanol to a second synthesis step, butadiene can be obtained with higher synthesis efficiency.

The molar ratio represented by ethanol/acetaldehyde (hereinafter, sometimes referred to as a EtOH/AcH ratio) in the primary product is preferably from 1/5 to 5/1. If the EtOH/AcH ratio is within the above range, the synthesis efficiency of butadiene from ethanol and acetaldehyde can be further enhanced.

The EtOH/AcH ratio in the primary product is easily adjusted by a combination of the composition of the first catalyst, the average pore diameter of the carrier of the first catalyst, the reaction temperature, the reaction pressure and the like. For example, if the reaction temperature is increased, the selectivity of ethanol is enhanced and the EtOH/AcH ratio increases.

It should be noted that although acetaldehyde may be separately prepared so as to satisfy the EtOH/AcH ratio, from the viewpoint of production efficiency, it is more preferable to use those obtained in the first synthesis step.

Usually, the primary product contains unreacted hydrogen and carbon monoxide, by-products such as acetic acid, methane and ethyl acetate.

The content of the aforementioned intermediate in the primary product (the amount of ethanol or the total amount of ethanol and acetaldehyde in the primary product) is not particularly limited, but is, for example, preferably 10% by mass or more, and more preferably 15% by mass or more. If the content of the aforementioned intermediate is equal to or more than the above lower limit value, the synthesis efficiency of butadiene can be further enhanced. The higher the content of the aforementioned intermediate in the primary product, the higher the synthesis efficiency of butadiene.

It should be noted that the content of the aforementioned intermediate in the primary product is easily adjusted by a combination of the composition of the first catalyst, the average pore diameter of the carrier of the first catalyst, the reaction temperature, the reaction pressure, and the like.

The primary product such as ethanol-containing gas flowing out from the first reaction tube 10 flows into the first purifier 20 via the pipe 14. The primary product flowed into the first purifier 20 is purified by removing substances other than ethanol and acetaldehyde. The removed substance is discharged from a discharge pipe 24 to the outside of the first purifier 20 (first purification step).

The purified primary product flows into the second reaction tube 30 via the pipe 22. The primary product flowed into the second reaction tube 30 flows through while coming into contact with the second catalyst of the second reaction bed 31, and a portion thereof becomes butadiene.

In this manner, the primary product flows through the second reaction bed 31 and becomes a secondary product containing butadiene. In the present embodiment, the secondary product is a gas. The secondary product flows out from the second reaction tube 30 (the processes up to this point constitute the second synthesis step). The secondary product flowed out from the second reaction tube 30 flows into a storage tank or the like (not shown) via a pipe 32.

The temperature (reaction temperature) at the time of bringing the primary product into contact with the second catalyst, in other words, the temperature of the second reaction bed 31 is, for example, preferably from 300 to 500° C., and more preferably from 350 to 450° C. If it is equal to or more than the above lower limit value, the rate of the catalytic reaction can be sufficiently increased, and butadiene can be produced more efficiently. If it is equal to or less than the above upper limit value, deterioration of the second catalyst can be suppressed.

The pressure (reaction pressure) at the time of bringing the primary product into contact with the second catalyst, in other words, the pressure inside the second reaction tube 30 is, for example, from atmospheric pressure to 1 MPa.

The space velocity of the primary product in the second reaction bed 31 is, in terms of the standard state, preferably from 1,000 to 50,000 L/L-catalyst/h, more preferably from 200 to 10,000 L/L-catalyst/h, and even more preferably from 300 to 5,000 L/L-catalyst/h. The space velocity is appropriately adjusted in consideration of the reaction pressure, the reaction temperature, and the composition of the mixed gas as a raw material.

The secondary product (butadiene-containing product) contains unreacted ethanol and acetaldehyde, and by-products.

Therefore, the method for producing butadiene may have a step (second purification step) of purifying the secondary product at a stage subsequent to the second synthesis step.

Examples of the second purification step include a step of treating the secondary product with a gas-liquid separator to separate butadiene and substances other than butadiene and recover butadiene.

In addition, the method for producing butadiene may have a step of liquefying the secondary product at a stage subsequent to the second synthesis step.

As described above, in the butadiene production method of the present embodiment, a gaseous primary product containing an intermediate such as ethanol is produced by the first synthesis step, and this gaseous primary product is brought into contact with the second catalyst. Therefore, a step of gasifying an intermediate such as ethanol becomes unnecessary, and the energy efficiency in the method for producing butadiene can be further enhanced.

In addition, when a primary product containing ethanol and acetaldehyde as an intermediate is produced by the first synthesis step, it is unnecessary to produce ethanol and acetaldehyde separately and to purify them separately. For this reason, energy efficiency in the butadiene production method can be further enhanced, as compared with the case of producing and purifying ethanol and acetaldehyde separately. In addition, the first synthesis step can adjust the EtOH/AcH ratio of the primary product to be suitable for the second synthesis step. Therefore, it is possible to increase the production efficiency of butadiene by supplying the primary product to the second synthesis step without adjusting the EtOH/AcH ratio of the primary product after the first synthesis step.

According to the butadiene production method of the present embodiment, the first purification step is provided between the first synthesis step and the second synthesis step. Therefore, substances that reduce the synthesis efficiency of butadiene in the second synthesis are removed from the primary product, and the synthesis efficiency of butadiene in the second synthesis step can be further improved.

The present invention is not limited to the embodiment described above.

In the embodiment described above, the primary product is obtained as a gas, and the primary product is allowed to flow into the second reaction tube as it is. However, the present invention is not limited thereto. For example, a primary product may be obtained as a gas in the first synthesis step, after which the primary product is condensed into a liquid, and then the primary product in the form of a liquid is gasified, and the gaseous primary product may be allowed to flow into the second reaction tube. However, from the viewpoint of enhancing the production efficiency of butadiene, it is preferable to cause the primary product obtained as a gas to flow into the second reaction tube as it is.

In the above embodiment, the first purifier is a membrane type separator, but the present invention is not limited thereto. The first purifier may be, for example, a gas-liquid separator, a distillation column or the like. However, from the viewpoint that the primary product is caused to flow into the second reaction tube without being liquefied and the production efficiency of butadiene can be further improved, as the first purifier, a membrane type separator capable of purifying the primary product as it is in a gaseous form is preferable.

EXAMPLES (Production Example 1) Production of First Catalyst (A)

1.22 mL of an aqueous solution (primary impregnation solution) containing 0.049 g of a titanium lactate ammonium salt $(Ti(OH)_2[OCH(CH_3)COO^-]_2(NH_4)_2)$ was prepared. 1.22 mL of the primary impregnating solution was added dropwise to 2.0 g of a porous carrier (material: silica, particle size: 1.18 to 2.36 mm, average pore diameter: 5.7 nm, total pore volume: 0.61 mL/g, specific surface area: 430 m$^2$/g) to impregnate the porous carrier with the primary impregnating solution (primary impregnation step). The porous carrier impregnated with the primary impregnating solution was dried for 3 hours at 110° C. (primary drying operation) and then further calcined for 4.5 hours at 400° C. (primary calcination operation) to produce a primary carrier (the processes up to this point constitute a primary loading step). 0.6 mL of an aqueous solution (secondary impregnating solution) containing 0.154 g of rhodium chloride trihydrate ($RhCl_3.3H_2O$), 0.087 g of manganese chloride dihydrate ($MnCl_2.2H_2O$) and 0.01 g of lithium chloride monohydrate ($LiCl.H_2O$) was prepared. 0.6 mL of the secondary impregnating solution was added dropwise and impregnated into the primary carrier (secondary impregnation step), and the resultant was dried for 3 hours at 110° C. (secondary drying operation), and then calcined for 4.5 hours at 400° C. (secondary calcination operation) to obtain a catalyst (A) (the processes up to this point constitute a secondary loading step).

In the total of the primary impregnating solution and the secondary impregnating solution, the molar ratios of the hydrogenation-active metals are rhodium:manganese=1:0.75, rhodium:lithium=1:0.275, and manganese:lithium=1:0.667.

(Production Example 2) Production of First Catalyst (B)

2.16 mL of an aqueous solution (primary impregnating solution) containing 0.123 g of a titanium lactate ammonium salt $(Ti(OH)_2[OCH(CH_3)COO^-]_2(NH_4)_2)$ was prepared. 2.16 mL of the primary impregnating solution was added dropwise to 2.0 g of a porous carrier (material: silica, particle size: 0.7 to 2.0 mm, average pore diameter: 13.7 nm, total pore volume: 1.1 mL/g, specific surface area: 310 m$^2$/g) to impregnate the porous carrier with the primary impregnating solution (primary impregnation step). The porous carrier impregnated with the primary impregnating solution was dried for 3 hours at 110° C. (primary drying operation) and then further calcined for 4.5 hours at 400° C. (primary calcination operation) to produce a primary carrier (the processes up to this point constitute a primary loading step). 0.6 mL of an aqueous solution (secondary impregnating solution) containing 0.154 g of a rhodium chloride trihydrate ($RhCl_3.3H_2O$), 0.032 g of manganese chloride dihydrate ($MnCl_2.2H_2O$), and 0.005 g of lithium chloride monohydrate ($LiCl.H_2O$) was prepared. 0.6 mL of the secondary impregnating solution was added dropwise and impregnated into the primary carrier (secondary impregnation step), and the resultant was dried for 3 hours at 110° C. (secondary drying operation), and then calcined for 4.5 hours at 400° C. (secondary calcination operation) to obtain a first catalyst (B) (the processes up to this point constitute a secondary loading step). In the total of the primary impregnating solution and the secondary impregnating solution, the molar ratios of the hydrogenation-active metals are rhodium:manganese=1:0.275, rhodium:lithium=1:0.138 and manganese:lithium=1:0.5.

Example 1

0.5 g of the first catalyst (A) obtained in Production Example 1 was filled into a cylindrical reaction tube made of stainless steel having a diameter of 1.5 inches (1.27 cm) and a length of 10 inches (25.4 cm) to form a first reaction bed.

The first catalyst (A) was subjected to a reduction treatment by heating for 2.5 hours at 320° C., while causing the hydrogen gas to flow through the first reaction bed at a rate of 30 mL/min at atmospheric pressure.

Then, a mixed gas (hydrogen: 60% by volume, carbon monoxide: 30% by volume, nitrogen: 10% by volume) was caused to flow through the first reaction bed at a space velocity of 14,400 L/L-catalyst/h under conditions of a reaction temperature of 286° C., and a reaction pressure of 2 MPa, to obtain an ethanol-containing gas (first synthesis step).

The mixed gas was caused to flow through the first reaction bed for 3 hours, the resulting ethanol-containing gas (gas) was recovered, and the composition of the ethanol-containing gas was analyzed by gas chromatography.

The CO conversion (mol %) and the selectivity of ethanol (mol %) were calculated from the obtained data, and the results are shown below.
CO conversion: 34.9 mol %.
Selectivity of ethanol: 40.1 mol %.
Selectivity of acetaldehyde: 27.7 mol %.

Example 2

0.5 g of the first catalyst (B) obtained in Production Example 2 was filled into a cylindrical reaction tube made of stainless steel having a diameter of 1.5 inches (1.27 cm) and a length of 10 inches (25.4 cm) to form a first reaction bed.

The first catalyst (B) was subjected to a reduction treatment by heating for 2.5 hours at 320° C., while causing the hydrogen gas to flow through the first reaction bed at a rate of 30 mL/min at atmospheric pressure.

Then, a mixed gas (hydrogen: 60% by volume, carbon monoxide: 30% by volume, nitrogen: 10% by volume) was caused to flow through the first reaction bed at a space velocity of 14,400 L/L-catalyst/h under conditions of a reaction temperature of 277° C. and the reaction pressure of 2 MPa to obtain a primary product (first synthesis step).

The mixed gas was caused to flow through the first reaction bed for 3 hours, the resulting primary product (gas) was recovered, and the composition of the primary product was analyzed by gas chromatography.

The CO conversion (mol %), the selectivity of ethanol (mol %) and the selectivity of acetaldehyde (mol %) were calculated from the obtained data, and the results are shown below.
CO conversion: 6.5 mol %.
Selectivity of ethanol: 35.9 mol %.
Selectivity of acetaldehyde: 15.4 mol %.

As described above, it was possible to obtain the primary product containing ethanol and acetaldehyde in Example 1 to which the present invention was applied. In addition, the EtOH/AcH ratio of the resulting primary product was suitable for the synthesis of butadiene.

(Production Example 3) Production of Butadiene Synthesis Catalyst (C)

8.351 mL of an aqueous solution (primary impregnating solution) containing 0.431 g of hafnium chloride ($HfCl_4$) was prepared. 8.351 mL of the primary impregnating solution was added dropwise to 2.0 g of a porous carrier (material: silica, particle diameter: 1.18 to 2.36 mm, average pore diameter: 16.3 nm, total pore volume: 0.99 mL/g, specific surface area: 195 $m^2$/g), and the porous carrier was impregnated with the primary impregnating solution (primary impregnation step). The porous carrier impregnated with the primary impregnating solution was dried for 3 hours at 110° C. (primary drying operation) and then further calcined for 4.5 hours at 400° C. (primary calcination operation) to produce a primary carrier (the processes up to this point constitute a primary loading step). 8.406 mL of an aqueous solution (secondary impregnating solution) containing 0.304 g of copper nitrate trihydrate ($Cu(NO_3)_2.3H_2O$) and 0.182 g of zinc nitrate hexahydrate ($Zn(NO_3)_2.6H_2O$) was prepared. 8.406 mL of the secondary impregnating solution was added dropwise and impregnated into the primary carrier (secondary impregnation step), and the resultant was dried for 3 hours at 110° C. (secondary drying operation), and then calcined for 4.5 hours at 400° C. (secondary calcination operation) to obtain a catalyst (C) (the processes up to this point constitute a secondary loading step).

In the total of the primary impregnating solution and the secondary impregnating solution, the molar ratios of the hydrogenation-active metals were copper:zinc=1.00:0.49, copper:hafnium=1.00:1.07 and zinc:hafnium=0.49:1.07.

Example 3

0.5 g of the first catalyst (A) obtained in Production Example 1 was filled into a cylindrical reaction tube made of stainless steel having a diameter of 1.5 inches (1.27 cm) and a length of 10 inches (25.4 cm) to form a first reaction bed. Furthermore, 3.5 g of the butadiene synthesis catalyst (C) obtained in Production Example 3 was filled into a cylindrical reaction tube made of stainless steel having a diameter of 1.5 inches (1.27 cm) and a length of 10 inches (25.4 cm) to form a second reaction bed.

The first catalyst (A) was subjected to a reduction treatment by heating for 2.5 hours at 320° C. while causing a hydrogen gas to flow through the first reaction bed at a rate of 30 mL/min at atmospheric pressure, and was then heated for 2.5 hours at 420° C., while causing a nitrogen gas to flow through the second reaction bed at a rate of 70 mL/min at atmospheric pressure.

Then, a mixed gas (hydrogen: 60% by volume, carbon monoxide: 30% by volume, nitrogen: 10% by volume) was caused to flow through the first reaction bed at a space velocity of 10,800 L/L-catalyst/h under conditions of a reaction temperature of 275° C. and a reaction pressure of 0.900 MPa, to obtain a primary product (first synthesis step). Subsequently, the resulting primary product (gas) as it is was caused to flow through the second reaction bed at atmospheric pressure to obtain a secondary product. The gas was caused to flow through the second reaction bed for 3 hours, the resulting secondary product (gas) was recovered, and the composition of the secondary product was analyzed by gas chromatography.

The CO conversion (mol %), the selectivity of ethanol (mol %) and the selectivity of acetaldehyde (mol %) were calculated from the obtained data, and the results are shown below.

CO conversion: 17.5 mol %.
Selectivity of BD: 12.1 mol %.

INDUSTRIAL APPLICABILITY

According to the present invention, it is possible to provide a method for producing butadiene and a device for producing butadiene capable of enhancing the energy efficiency and the production efficiency of butadiene.

REFERENCE SIGNS LIST

1: Butadiene production device;
10: First reaction tube;
20: First purifier;
30: Second reaction tube;

The invention claimed is:

1. A method for producing butadiene, the method comprising:
a first synthesis step of bringing a mixed gas containing hydrogen and carbon monoxide into contact with a first catalyst to obtain a primary product as a gas containing ethanol as an intermediate;
a second synthesis step of bringing the primary product as the gas into contact with a second catalyst to obtain butadiene; and
a first purification step of removing a substance other than the intermediate from the primary product by an apparatus equipped with a separation membrane between the first synthesis step and the second synthesis step.

2. The method according to claim 1, wherein the primary product further comprises acetaldehyde as an intermediate.

3. The method according to claim 2, wherein the primary product has a molar ratio represented by ethanol/acetaldehyde of 5/1 to 1/5.

4. A device for producing butadiene, the device comprising:
a first reaction tube filled with a first catalyst;
a second reaction tube filled with a second catalyst; and
an apparatus equipped with a separation membrane between the first reaction tube and the second reaction tube,
wherein the first catalyst synthesizes a primary product as a gas containing ethanol or ethanol and acetaldehyde as an intermediate from a mixed gas containing hydrogen and carbon monoxide;
the second catalyst synthesizes butadiene from the intermediate;
the second reaction tube is provided downstream of the first reaction tube and brings the primary product as the gas into contact with the second catalyst; and
the apparatus equipped with the separation membrane removes a substance other than the intermediate from the primary product.

* * * * *